(12) United States Patent
Thomas et al.

(10) Patent No.: US 7,598,378 B2
(45) Date of Patent: Oct. 6, 2009

(54) METHOD FOR THE PRODUCTION OF 4-(4-AMINOPHENYL)-3-MORPHOLINONE

(75) Inventors: Christian Thomas, Wuppertal (DE); Mathias Berwe, Sprockhövel (DE); Alexander Straub, Wuppertal (DE)

(73) Assignee: Bayer Schering Pharma AG (DE)

( * ) Notice: Subject to any disclaimer, the term of this patent is extended or adjusted under 35 U.S.C. 154(b) by 659 days.

(21) Appl. No.: 10/571,364

(22) PCT Filed: Sep. 9, 2004

(86) PCT No.: PCT/EP2004/010054
§ 371 (c)(1), (2), (4) Date: Mar. 9, 2006

(87) PCT Pub. No.: WO2005/026135
PCT Pub. Date: Mar. 24, 2005

(65) Prior Publication Data
US 2007/0066611 A1    Mar. 22, 2007

(30) Foreign Application Priority Data
Sep. 15, 2003  (DE) ................. 103 42 570

(51) Int. Cl.
*C07D 413/14* (2006.01)
*C07D 295/135* (2006.01)
(52) U.S. Cl. ...................... 544/139; 544/166
(58) Field of Classification Search .......... 544/139, 544/166
See application file for complete search history.

(56) References Cited

FOREIGN PATENT DOCUMENTS

| WO | WO 01/47919 A1 | 7/2001 |
|---|---|---|
| WO | WO 02/064575 A1 | 8/2002 |
| WO | WO 03/000256 A1 | 1/2003 |
| WO | WO 2004/101553 A1 | 11/2004 |
| WO | WO 2004/101556 A1 | 11/2004 |

*Primary Examiner*—Rebecca L Anderson
(74) *Attorney, Agent, or Firm*—Edwards Angell Palmer & Dodge LLP; Barry Kramer; Ralph A. Loren

(57) ABSTRACT

The present invention relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

10 Claims, No Drawings

METHOD FOR THE PRODUCTION OF 4-(4-AMINOPHENYL)-3-MORPHOLINONE

The present invention relates to a process for preparing 4-(4-aminophenyl)-3-morpholinone by reacting 4-(4-nitrophenyl)-3-morpholinone with hydrogen in the presence of a hydrogenation catalyst, characterized in that the reaction is effected in an aliphatic alcohol.

4-(4-Aminophenyl)-3-morpholinone is a central precursor in the synthesis of 5-chloro-N-({(5S)-2-oxo-3-[4-(3-oxo-4-morpholinyl)phenyl]-1,3-oxazolidin-5-yl}methyl)-2-thiophenecarboxamide, an inhibitor of the blood clotting factor Xa, which can be used for the prophylaxis and/or treatment of various thromboembolic disorders (on this subject, see WO-A 01/47919, whose disclosure-content is hereby incorporated by reference).

5-Chloro-N-({(5S)-2-oxo-3-[4-(3-oxo-4-morpholinyl)phenyl]-1,3-oxazolidin-5-yl}methyl)-2-thiophenecarboxamide (IV) is synthesized according to WO-A 01/47919 starting from 4-(4-aminophenyl)-3-morpholinone (I), 2-[(2S)-2-oxiranylmethyl]-1H-isoindole-1,3(2H)-dione (II) and 5-chlorothiophene-2-carbonyl chloride (III):

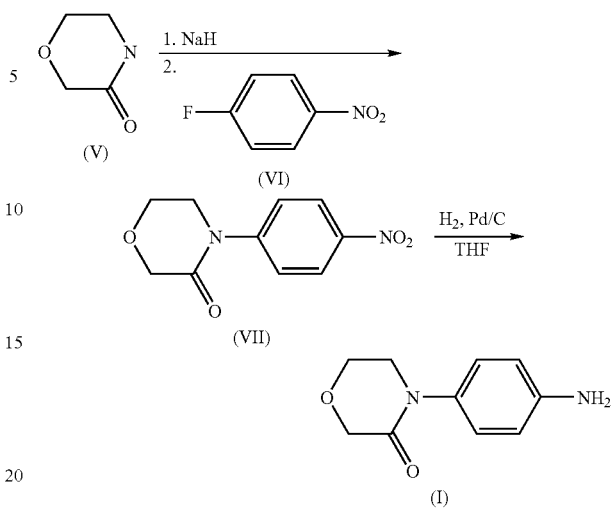

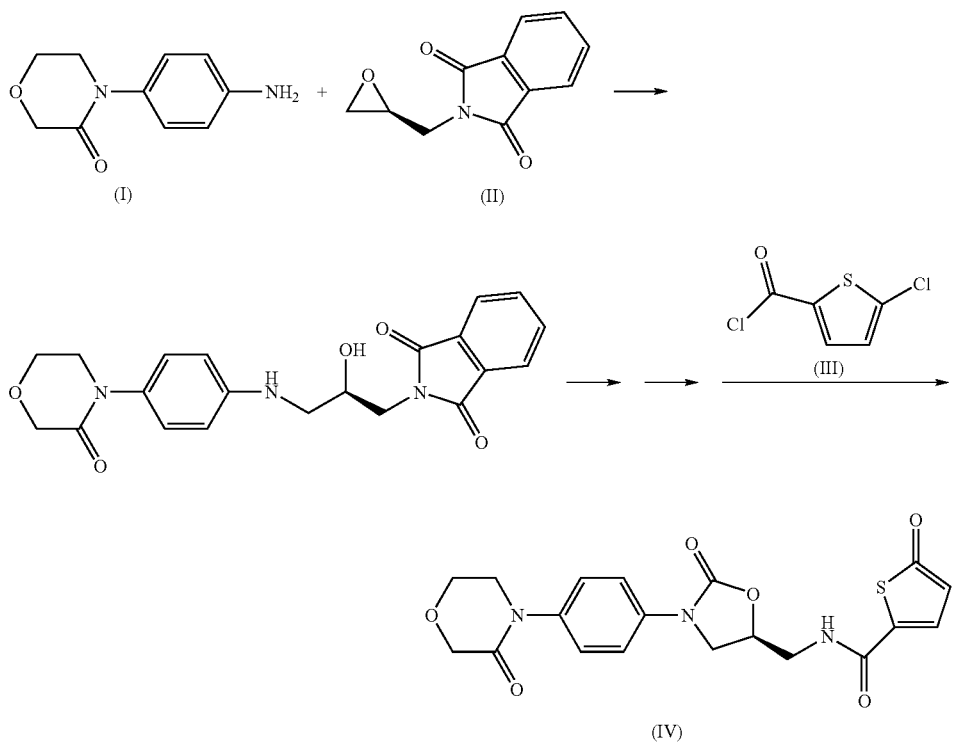

WO-A 02/48099 likewise describes 4-(4-aminophenyl)-3-morpholinone as a precursor for the synthesis of active ingredients, but there is no information there whatsoever on the preparation of this compound.

In contrast, WO-A 01/47919 also describes a preparation method for 4-(4-aminophenyl)-3-morpholinone (I). In this method, morpholin-3-one (V) is first deprotonated with sodium hydride and then reacted with 4-fluoronitrobenzene (VI) to give 4-(4-nitrophenyl)-3-morpholinone (VII). Catalytic hydrogenation of (VII) with hydrogen over palladium on activated carbon in tetrahydrofuran as a solvent affords 4-(4-aminophenyl)-3-morpholinone (I):

However, the yield of this process at 17.6% of theory in the first stage and 37.6% of theory in the second stage is unsatisfactory. In the second stage, the hydrogenation of the nitro group of (VII), one reason for this low yield will certainly be the drastic reaction conditions, specifically eight hours of reaction time at 70° C. and a hydrogen pressure of 50 bar. Moreover, the high pressure entails considerable apparatus complexity. The resulting product also has to be purified by crystallization. These disadvantages complicate the reaction on a larger scale in particular.

This gives rise to the object of the present invention, of providing a simplified process for preparing 4-(4-aminophenyl)-3-morpholinone (I) which is suitable especially for the preparation of relatively large amounts.

It has been found that, surprisingly, the reaction of 4-(4-nitrophenyl)-3-morpholinone (VII) with hydrogen can be carried out in the presence of a hydrogenation catalyst, preferably palladium on activated carbon (5%), in aliphatic alcohols, preferably in alcohols having 1 to 4 carbon atoms such as methanol, ethanol or n-butanol. The reaction more preferably takes place in ethanol, in solution or in suspension. The use of ethanol as the solvent at temperatures between 40 and 120° C., preferably 75 to 85° C., and a hydrogen pressure of 2 to 10 bar, preferably 4.5 to 5.5 bar, can distinctly shorten the reaction time. In general, the reaction is complete after only about one hour. These mild reaction conditions lead to the product (I) being obtained in excellent yield and in high purity.

In the case of ethanol as the solvent, the reaction mixture is worked up merely by admixing with water and ethanol and filtering off the catalyst from the product solution at 40° C. 4-(4-Aminophenyl)-3-morpholinone (I) is isolated by concentration of the filtrate under reduced pressure. When other solvents are used, the workup conditions are adjusted appropriately.

In a preferred embodiment, the product-containing filtrate is reacted further directly without isolating 4-(4-aminophenyl)-3-morpholinone (I) in substance.

In the present invention, differently to the description in WO-A 01/47919, 4-(4-nitrophenyl)-3-morpholinone (VII) is prepared by nitrating 4-phenyl-3-morpholinone (VIII).

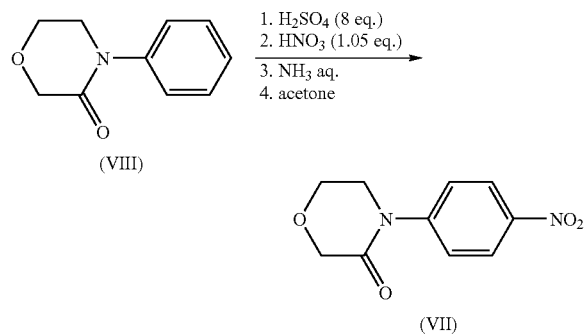

In this reaction, 4-phenyl-3-morpholinone (VIII) is added at an internal temperature of 5 to 15° C. in portions to 7 to 8 equivalents of concentrated sulphuric acid and the mixture is then stirred at 25° C. for approx. 30 minutes. Subsequently, the reaction mixture is admixed at −10 to 0° C. with 0.9 to 1.2 equivalents of 65% nitric acid. As is frequently the case in nitrations, this forms not only the desired para-isomer but also the undesired ortho- and meta-isomers. For workup, water and 25% aqueous ammonia solution are added at 5 to 15° C. to the reaction mixture until a pH of 7 to 7.5 has been attained.

It has been found that, surprisingly, the desired para-isomer (VII), after addition of acetone and heating of the reaction mixture to 40° C., is dissolved selectively in the organic phase and can be removed by extraction in a simple and advantageous manner in this way.

The concentration of the organic phase crystallizes the product (VII) out of the acetone/water mixture, thus allowing it to be isolated.

For the preparation of 4-phenyl-3-morpholinone (VIII), the literature describes various syntheses:

According to U.S. Pat. No. 3,092,630, 1,4-dioxan-2-one and aniline are reacted in an autoclave at 340° C. to obtain a certain but unspecified amount of (VIII).

J. Heterocycl. Chem. 2000, 37, 109-110 describes the preparation of (VIII) by phase transfer-catalysed oxidation of 4-phenylmorpholine with potassium permanganate. However, a further reaction product formed here is readily ignitable manganese dioxide. Furthermore, the yield is only 45% of theory and the reaction can be carried out on a larger scale only with difficulty.

The reaction of ethyl 2-chloroacetate with 2-anilinoethanol is described in Bull. Soc. Chim. France 1956, 1210-1212 and also in Zhurnal Organicheskoi Khimii 1970, 6, 1305-1308 [CA 73:66523]. However, the deprotonation is effected here with sodium in toluene and in benzene respectively.

The drastic reaction conditions described in the prior art, or reaction conditions, reagents or solvents which are technically difficult to handle, can be avoided by, in accordance with the invention, preparing 4-phenyl-3-morpholinone (VIII) by reaction of chloroacetyl chloride with 2-anilinoethanol.

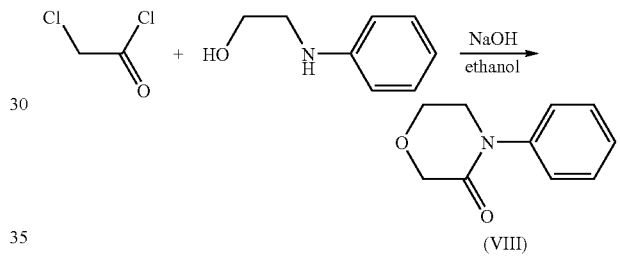

This process is in particular efficiently employable even on an industrial scale. In this process, 2-anilinoethanol is initially charged in aqueous alcoholic, preferably ethanolic, solution. 2.5 to 3.5 equivalents of chloroacetyl chloride and 4 to 8, preferably 5 to 7, equivalents of base are metered in simultaneously. The bases used are alkali metal or alkaline earth metal hydroxide solutions, preferably sodium hydroxide or potassium hydroxide solutions, in particular aqueous sodium hydroxide solution. The addition is effected at an internal temperature of the reaction solution of 30 to 50° C., preferably of 35 to 45° C. The rate of addition is also adjusted such that the pH of the reaction solution is between 10 and 13.5, preferably between 12 and 12.5.

After the reaction solution has been cooled to 0 to 10° C., the product (VIII) crystallizes out and can be obtained in good yield and high purity by filtration and washing with cold water.

The present invention further provides 4-(4-aminophenyl)-3-morpholinone prepared in accordance with the invention.

The present invention further provides for the use of 4-(4-aminophenyl)-3-morpholinone prepared in accordance with the invention for preparing 5-chloro-N-({(5S)-2-oxo-3-[4-(3-oxo-4-morpholinyl)phenyl]-1,3-oxazolidin-5-yl}methyl)-2-thiophenecarboxamide (IV).

The invention is illustrated in detail below by a preferred working example, to which it is not, however, restricted. Unless stated otherwise, all amounts reported are percentages by weight.

Synthesis of 4-(4-aminophenyl)-3-morpholinone (I)

1st Step: 4-phenyl-3-morpholinone (VIII)

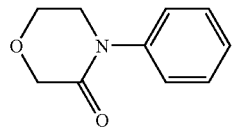

In a 26-liter tank, 1.65 kg (12.0 mol) of 2-anilinoethanol are dissolved at room temperature in 1.53 l of ethanol and subsequently admixed with 4.58 l of water with stirring. The solution is heated to 38° C. 4.07 kg (3.0 equivalents) of chloroacetyl chloride and 6.60 kg of 45% sodium hydroxide solution (6.2 equivalents) are then added simultaneously at an internal temperature of 38 to 43° C. within 60 to 80 minutes, so that the pH is kept between 12 and 12.5. The mixture is stirred at a pH of 12 to 12.5 for 10 minutes, then cooled to 2° C. and stirred at this temperature for 30 minutes. The precipitated product is filtered off and washed twice with 3.3 kg each time of demineralized water at 2° C. The moist product is dried to constant mass at 50° C. under reduced pressure.

Yield: 1700 g (80% of theory) of a white solid. Melting point: 114° C.

2nd Step: 4-(4-nitrophenyl)-3-morpholinone (VII)

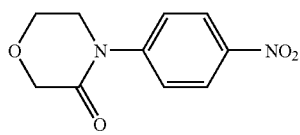

In a 2-liter flask, 177 g (1.0 mol) of 4-phenyl-3-morpholinone (VIII) are introduced at internal temperature 10° C. in 4 portions into 728 g (7.4 equivalents) of concentrated sulphuric acid. The mixture is then heated to 25° C. and stirred at this temperature for 30 minutes. The solution is cooled to −5° C. and admixed within one hour with 101.8 g (1.05 equivalents) of 65% nitric acid. The mixture is stirred at −5° C. for one hour. 1300 ml of demineralized water are metered into this solution at 10° C. Subsequently, a pH of 7.4 is established, likewise at 10° C., with 25% aqueous ammonia solution. The suspension is admixed with 2000 g of acetone and heated to 40° C. In the course of this, the product goes into solution, so that the phases can be separated. 1500 g of acetone/water mixture are distilled off at standard pressure from the organic phase, in the course of which the product precipitates out. The suspension is cooled to 10° C. and stirred for a further 30 minutes, and the product is isolated. The moist product is washed with 320 g of cold acetone and dried at 50° C. under reduced pressure.

Yield: 157 g (70% of theory) of a white solid. Melting point: 152° C.

3rd Step: 4-(4-aminophenyl)-3-morpholinone (I)

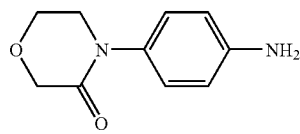

60 g (0.27 mol) of 4-(4-nitrophenyl)-3-morpholinone (VII) are suspended in 480 g of ethanol, admixed with 3 g of palladium on activated carbon (5%) and contacted with 5 bar of hydrogen at 80° C. for one hour. After hydrogenation has ended, the suspension is admixed with 80 g of ethanol and 270 g of water and heated to 40° C., and the catalyst is filtered off. The solution is concentrated under reduced pressure and the remaining solid is dried to constant weight at 50° C. under reduced pressure.

Yield: 48.4 g (93% of theory) of a white to slightly reddish-coloured solid. Melting point: 171° C.

The invention claimed is:

1. A process for preparing 4-(4-aminophenyl)-3-morpholinone comprising reacting 4-(4-nitrophenyl)-3-morpholinone with hydrogen in the presence of a hydrogenation catalyst, the reaction being effected in an aliphatic alcohol.

2. The process for preparing 4-(4-aminophenyl)-3-morpholinone according to claim 1, wherein the aliphatic alcohol is ethanol.

3. The process for preparing 4-(4-aminophenyl)-3-morpholinone according to claim 1 or 2, characterized in that said 4-(4-nitrophenyl)-3-morpholinone is prepared by nitrating 4-phenyl-3-morpholinone.

4. The process according to claim 3, wherein the 4-(4-nitrophenyl)-3-morpholinone prepared by nitration is worked up by extraction with acetone.

5. The process according to claim 4, wherein the 4-(4-nitrophenyl)-3-morpholinone is isolated by crystallization from an acetone/water mixture after the extraction.

6. The process according to claim 3, wherein 4-phenyl-3-morpholinone is prepared by reacting 2-anilinoethanol with chloroacetyl chloride.

7. The process according to claim 6, wherein chloroacetyl chloride and base are metered in simultaneously.

8. The process according to claim 7, wherein the base is aqueous sodium hydroxide solution.

9. The process according to claim 8, wherein chloroacetyl chloride and sodium hydroxide solution are added at an internal temperature of 35 to 45°C. and while maintaining a pH of the reaction solution between 12 and 12.5.

10. A process for preparing 5-chloro-N-({(5S)-2-oxo-3-[4-(3-oxo-4-morpholinyl)phenyl]-1,3-oxazolidin-5-yl}methyl)-2-thiophenecarboxamide, comprising first reacting 4-(4-aminophenyl)-3-morpholinone prepared according to claim 1 with 2-[(2S)-2-oxiranylmethyl]-1H-isoindole-1,3 (2H)-dione and subsequently reacting the initial reaction product with 5-chlorothiophene-2-carbonyl chloride.

* * * * *